United States Patent [19]
Knutsen et al.

[11] Patent Number: 5,672,588
[45] Date of Patent: Sep. 30, 1997

[54] PURINE DERIVATIVES

[75] Inventors: Lars Jacob Stray Knutsen, Vedbæk; Jesper Lau, Farum, both of Denmark

[73] Assignee: Novo Nordisk A/S, Bagsvaerd, Denmark

[21] Appl. No.: 521,077

[22] Filed: Aug. 28, 1995

Related U.S. Application Data

[63] Continuation of Ser. No. 348,785, Dec. 2, 1994, abandoned, which is a continuation of Ser. No. 60,784, May 12, 1993, abandoned, which is a continuation-in-part of Ser. No. 886,534, May 20, 1992, abandoned.

[51] Int. Cl.$^6$ .............................. A61K 31/70; C07H 19/16
[52] U.S. Cl. .................. 514/46; 514/45; 514/929; 536/27.21; 536/27.6; 536/27.61; 536/27.62; 536/27.63; 536/27.7
[58] Field of Search ............... 536/27.21, 27.6, 536/27.61, 27.62, 27.63, 27.7; 514/45, 46, 929

[56] References Cited

U.S. PATENT DOCUMENTS

| | | |
|---|---|---|
| 3,502,649 | 3/1970 | Thiel et al. . |
| 3,551,409 | 12/1970 | Kampe et al. . |
| 3,590,029 | 6/1971 | Koch et al. . |
| 5,032,583 | 7/1991 | Evans . |

FOREIGN PATENT DOCUMENTS

| | | |
|---|---|---|
| 0322242 | 6/1989 | European Pat. Off. . |
| 1123245 | 8/1968 | United Kingdom . |
| 1143150 | 2/1969 | United Kingdom . |

OTHER PUBLICATIONS

Kusachi et al., J. Med. Chem., vol. 29, pp. 989–996 (1986).
Daly et al., Biochemical Pharmacology, vol. 35, No. 15, pp. 2467–2481 (1986).

*Primary Examiner*—James O. Wilson
*Attorney, Agent, or Firm*—Steve T. Zelson, Esq.; Elias J. Lambiris, Esq.

[57] ABSTRACT

A compound of formula (I), or a pharmaceutically acceptable salt thereof:

wherein X is hydrogen, amino, halogen, hydroxy, lower alkoxy or lower alkyl and
$R^1$ is wherein Y is methylene or a valence bond,
$R^2$ and $R^5$ is H or lower, straight or branched alkyl,
$R^3$ is H or lower alkyl, or
$R^2$ and $R^3$ can together form a cyclobutyl, cyclopentyl, cyclohexyl or phenyl ring,
Z is oxygen, methylene, sulphur, sulphonyl or a valence bond,
$R^4$ is H, lower alkyl, aralkyl, a mono or bicyclic aromatic system optionally substituted with various groups.

The compounds have been found useful for treating central nervous system ailments.

12 Claims, No Drawings

PURINE DERIVATIVES

This application is a continuation of application Ser. No. 08/348,785 filed Dec. 2, 1994 now abandoned, which is a continuation application of application Ser. No. 08/060,784, filed May 12, 1993 now abandoned, which is a continuation-in-part of Ser. No. 07/886,534 filed May 20, 1992, now abandoned, the contents of which are incorporated herein by reference.

The present invention relates to a method for treating ischaemia, epilepsy and pain, to compounds for use in such a method and to pharmaceutical compositions containing the said compounds.

BACKGROUND OF THE INVENTION

Adenosine can be considered to be a hormone which has been shown to have a number of significant effects on the mammalian central nervous system (CNS) [Annual Reports in Medicinal Chemistry, 1988, 23, 39–48; International Review of Neurobiology (Smythies, J. R. and Bradley, R. J., eds.) Academic Press Inc., 1985, 27, 63–139], especially under conditions of neuronal stress where the compound appears to act as an endogenous neuroprotectant (Progress in Neurobiology, 1988, 31, 85–108, Trends in Pharmacological Sciences, 1988, 9, 193–194). For example, the concentration of adenosine has been demonstrated to rise greatly in certain brain regions following epileptic seizures or conditions of neuronal ischaemia/anoxia (Brain Research 1990, 516, 248–256).

It has been established for some years now that centrally acting adenosine receptor agonists or compounds which increase extracellular adenosine levels can exhibit what is termed neuromodulator activity. Such substances influence the release of neurotransmitters in regions of the central nervous system (Annual Review of Neuroscience, 1985, 8, 103–124; Trends in Neurosciences, 1984, 164–168), with particular inhibitory effects on the release of the excitatory amino acid glutamic acid (glutamate)(Nature, 1985, 316, 148–150, Journal of Neurochemistry, 1992, 58, 1683–1689).

There are several CNS ailments for which this adenosine receptor mediated neuromodulator activity could be of clear therapeutic benefit. Examples of these would include the treatment of convulsive disorders (European Journal of Pharmacology, 1991, 195, 261–265; Journal of Pharmacology and Experimental Therapeutics, 1982, 220, 70–76), prevention of neurodegeneration under conditions of brain anoxia/ischaemia (Neuroscience Letters, 1987, 83, 287–293; Neuroscience, 1989, 30, 451–462; Pharmacology of Cerebral Ischaemia 1990, (Kriegelstein, J. and Oberpichler, H., Eds., Wissenschaftliche Verlagsgesellschaft mbH: Stuttgart, 1990, pp 439–448) or the use of a purinergic agent in the treatment of pain (European Journal of Pharmacology, 1989, 162, 365–369; Neuroscience Letters, 1991, 121, 267–270).

Adenosine receptors represent a subclass (P1) of the group of purine nucleotide and nucleoside receptors known as purinoreceptors. This subclass has been further classified into two distinct receptor types which have become known as A1 and A2. Extensive research has been carried out in a quest to identify selective ligands at these sites [see, for example, Comprehensive Medicinal Chemistry, Volume 3, (Hansch, C., Sammes, P. G. and Taylor, J. B., Eds., Pergamon Press PLC: 1990, pp 601–642)]. Selective ligands exist for A1 and A2 adenosine receptors and the structure-activity relationships of the various reference ligands have been reviewed (Biochemical Pharmacology, 1986, 35, 2467–2481) together with their therapeutic potential (Journal of Medicinal Chemistry, 1992, 35, 407–422). Among the known adenosine receptor agonists most selective for the A1 receptor over the A2 receptor are the examples where the adenine nucleus is substituted with a cycloalkyl group on the amino function, for example N-cyclopentyladenosine and N-cyclohexyladenosine (Journal of Medicinal Chemistry, 1985, 28, 1383–1384) or 2-chloro-N-cyclopentyladenosine (Naunyn-Schmiedeberg's Arch. Pharmacol. 1988, 337, 687–689).

However, these ligands are found to possess undesirable effects as to influence upon the cardiovascular system, rendering them unsuitable for the treatment of CNS disorders such as cerebral ischaemia, epilepsy and pain.

GB 1,143,150 (equivalent to U.S. Pat. No. 3,551,409) and GB 1,123,245 disclose a number of adenosine derivatives, having interesting cardiac and circulatory actions.

In EP 322,242A, a new use, as "agents to reduce plasma free fatty acid concentration or reducing heart rate and condition" is claimed for the compounds listed below as well as physiologically acceptable salts and solvates thereof:

N-[(1S, trans)-2-hydroxycyclopentyl]adenosine
N-[(1R, trans)-2-hydroxycyclopentyl]adenosine
N-[(trans)-4-hydroxycyclohexyl]-2-methyladenosine
N-[(cis)-4-hydroxycyclohexyl]adenosine
N-[(cis)-2-hydroxycyclopentyl]adenosine
N-[(trans)-3-hydroxycyclohexyl]adenosine
N-[2β-hydroxy-2-methylcyclopentyl]adenosine and
N-[(cis)-2-hydroxycyclohexyl]adenosine

DESCRIPTION OF THE INVENTION

It has now been discovered that a selected group of adenosine derivatives, some of which are claimed in GB 1,143,150, has potential therapeutic utility for treating central nervous system ailments such as cerebral ischaemia, epilepsy and pain in humans. They have a clear CNS effect in relevant animal models at the same time as having a superior side-effect profile with respect to cardiovascular properties. In addition, the compounds have utility within myocardial ischaemia. Specifically, the following compounds possess therapeutic utility within the above-mentioned CNS indications:

2-Chloro-N-(1-phenoxy-2-propyl)adenosine
2-Chloro-N-[(R)-1-phenoxy-2-propyl]adenosine
2-Chloro-N-[(S)-1-phenoxy-2-propyl]adenosine
2-Chloro-N-(2-phenoxyethyl)adenosine
2-Chloro-N-[(R)-1-phenyl-2-propyl]adenosine
2-Chloro-N-(1-phenyl-3-butyl)adenosine
N-(1-Phenoxy-2-propyl)adenosine
2-Amino-N-(1-phenoxy-2-propyl)adenosine
N-[(1S, trans)-2-Hydroxycyclopentyl]adenosine
N-[(1R, trans)-2-Hydroxycyclopentyl]adenosine
2-Chloro-N-(cis-2-phenoxycyclopentyl)adenosine
trans-2-Chloro-N-(2-phenoxycyclopentyl)adenosine
2-Chloro-N-[(R)-1-hydroxy-2-propyl]adenosine
2-Chloro-N-[(R)-1-phenylthio-2-propyl]adenosine
2-Chloro-N-[(R)-1-(4-fluorophenoxy)-2-propyl]adenosine
2-Chloro-N-[(R)-2-phenoxy-1-propyl]adenosine
2-Chloro-N-[2-(phenylmethoxy)ethyl]adenosine
2-Fluoro-N-[(R)-1-phenoxy-2-propyl]adenosine
2-Methoxy-N-[(R)-1-phenoxy-2-propyl]adenosine
N-(2-Methoxyethyl)adenosine
2-Chloro-N-[(2-methoxyphenyl)methyl]adenosine
2-Chloro-N-[(R)-3-methyl-1-phenoxy-2-butyl]adenosine
2-Chloro-N-[(R)-1-(2-(2-propyloxy)phenoxy)-2-propyl]adenosine 2-Chloro-N-[(R)-1-phenylsulphonyl-2-propyl]adenosine
N-[(2-methylphenyl)methyl]adenosine
2-Methyl-N-[(R)-1-phenoxy-2-propyl]adenosine Accordingly, the present invention relates to adenosine analogues of formula I

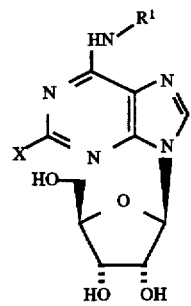

wherein X is hydrogen, amino, halogen, hydroxy, lower alkoxy or lower alkyl and
$R^1$ is

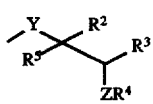

wherein Y is methylene or a valence bond, $R^2$ and $R^5$ is H or lower, straight or branched alkyl, $R^3$ is H or lower alkyl, or $R^2$ and $R^3$ can together form a cyclobutyl, cyclopentyl, cyclohexyl or phenyl ring, Z is oxygen, methylene, sulphur, sulphonyl or a valence bond, $R^4$ is H, lower alkyl, aralkyl a mono or bicyclic aromatic system optionally substituted with halogen, hydroxy, haloalkyl, alkyl, alkoxy, aryloxy, acyloxy or alkylmercapto radicals, or a pharmaceutically acceptable salt thereof as these compounds have been found useful in treatment of a number of CNS-related ailments, such as cerebral ischaemia, epilepsy and pain.

Further, the compounds of formula (I) are found to be useful agents, for lowering plasma free fatty acid (FFA) levels, as cardiovascular agents and also have application to myocardial ischaemia.

The invention also relates to methods of preparing the above mentioned compounds. These methods comprise:

Method A

A compound of formula (I) may be prepared by reacting a substance of formula (II), wherein L represents a leaving group such as a halogen atom (e.g. a chlorine or bromine atom) or a trimethylsilyloxy group, $P^1$, $P^2$ and $P^3$ are the same or different and represent hydrogen or a protecting group such as benzoyl-, p-toluoyl-, lower alkanoyl-(e.g. acetyl-), a substituted silyl group (e.g. a trimethylsilyl or t-butyldimethylsilyl group) or in the case of $P^3$, a triarylmethyl group, or in the case of $P^1$ and $P^2$, a 2',3'-O-(1-methyl)ethylidene function, with a substituted amine of general formula (III)

General process (A)

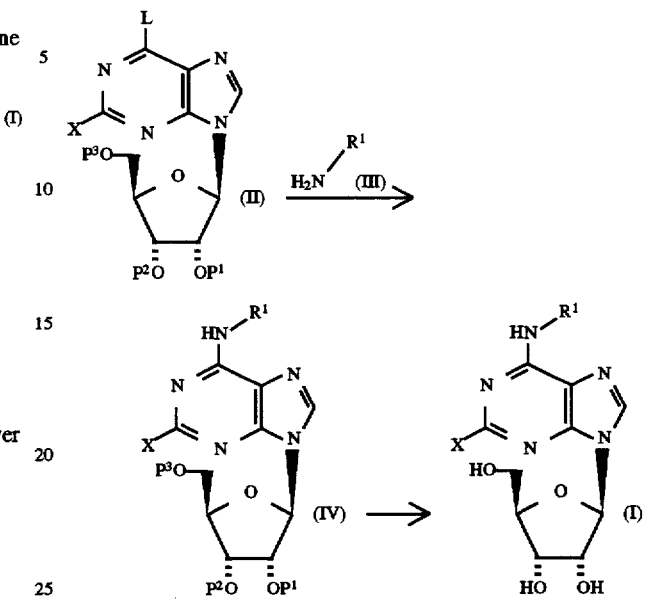

giving the compound of formula (IV) as the reaction product. In cases where $P^1$, $P^2$ and $P^3$ are not hydrogen an additional step will be required to remove protecting groups from (IV); in cases where the groups $P^1$, $P^2$ and $P^3$ are for example acetyl or benzoyl, suitable conditions for deprotection include the use of methanolic ammonia, an alkali metal carbonate in methanol, or an alkali metal alkoxide in the corresponding alcohol. Where the protecting groups are for example alkylsilicon or arylsilicon derivatives, suitable methods for deprotection include, for example, treatment with tetraalkylammonium fluorides or aqueous hydrolysis in the presence of acid or base. Where the $P^1$ and $P^2$ groups comprise a 2',3'-O-(1-methyl)ethylidene function or $P^3$ comprises triarylmethyl, suitable conditions for deprotection include, for example, hydrolysis with aqueous mineral acid.

Method B

A compound of formula (I) wherein X represents —NH$_2$, O-alkyl or hydroxy, may be prepared by reacting a substance of general formula (V)

General process (B)

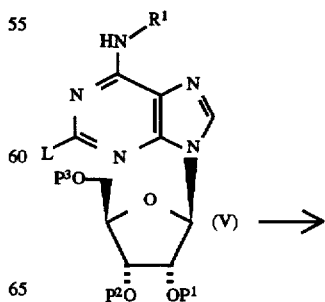

-continued
General process (B)

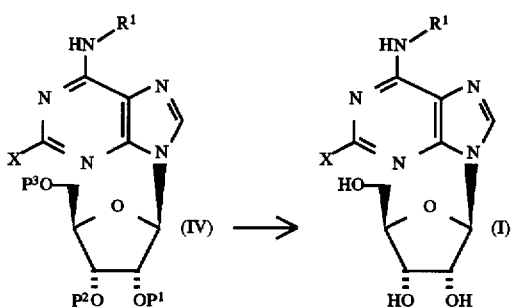

[where L is a leaving group as defined in method (A)] with a nucleophile, for example, ammonia or with an anion (e.g. $C_{1-6}$-alkoxide) to afford the product (IV). In cases where $P^1$, $P^2$ and $P^3$ are hydrogen, compound (I) can be obtained directly. However, in cases where $P^1$, $P^2$ and $P^3$ are not hydrogen an additional step will be involved to remove protecting groups from (IV); examples of conditions for removal of protecting groups are given in process (A). In some reactions involving (V) with the anion $C_{1-6}$-alkoxide, where $P^1$, $P^2$ and/or $P^3$ are for example acetyl- or benzoyl-, partial or full deprotection may take place. In cases where only partial deprotection has taken place, deprotection can be completed under conditions described in method (A).

Accordingly, the present invention provides a method for treating cerebral ischaemia, epilepsy and pain in human or non-human animals, which method comprises administering an effective, non-toxic amount of a compound of formula I or a pharmaceutically acceptable salt thereof, to human or non-human animals suffering from cerebral ischaemia, epilepsy or pain. The present invention also provides the use of a compound of formula I or a pharmaceutically acceptable salt thereof in the preparation of a medicament for use in the treatment of cerebral ischaemia, epilepsy or pain.

The present invention further provides a pharmaceutical composition for use in the treatment of cerebral ischaemia, epilepsy or pain which comprises an effective amount of a compound of formula I of a pharmaceutically acceptable salt thereof and a pharmaceutically acceptable carrier. Such compositions may be prepared in the manner as described below.

Various salts of compounds of formula (I) can be prepared which can be considered physiologically acceptable. These include addition salts derived from inorganic or organic acids, for example, acetates, fumarates, glutarates, glutaconates, lactates, maleates, methanesulphonates, phosphates, salicylates, succinates, sulphates, sulphamates, tartrates and paratoluene-sulphonates. In some cases, solvates of either the free nucleosides or the acid addition salts can be isolated and these solvates may, for example, be hydrates or alcoholates.

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets of filled capsules, or liquids, such as solutions, suspensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of the adenosine receptor agonist commensurate with the intended daily dosage range to be employed.

The compounds of this invention can thus be used for the formulation of pharmaceutical preparations. e.g. for oral and parenteral administration to mammals including humans, in accordance with conventional methods of galenic pharmacy. Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhyroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05–100 mg in a pharmaceutically acceptable carrier per unit dosage. The dosage of the compounds according to this invention is 0.1–300 mg/day, preferably 10–100 mg/day, when administered to patients, e.g. humans, as a drug.

A typical tablet which may be prepared by conventional tabletting techniques contains:
Active compound 5.0 mg
Lactosum 67.8 mg Ph.Eur.
Avicel® 31.4 mg
Amberlite®IRP 88 1.0 mg
Magnesii stearas 0.25 mg Ph.Eur.

Owing to activity against pain or convulsive disorders and prevention of neurodegeneration under conditions of anoxia/ischaemia the compounds of the invention are extremely useful in the treatment of related symptoms in mammals, when administered in an amount effective for agonist activity of compounds of the invention. The compounds of the invention may accordingly be administered to a subject, e.g., a living animal body, including a human, in need of an adenosine receptor agonist, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultanously, or together with a pharmaceutically-acceptable carrier or diluent, especially and preferably in the form of a pharmaceutical composition thereof, whether by oral, rectal, or parenteral (including subcutaneous) route, in an effective amount of adenosine receptor agonist, and in any event an amount which is effective for the treatment of anoxia, traumatic injury, ischemia, migraine or other pain symptoms, epilepsy, or neurodegenerative diseases owing to their adenosine receptor agonist activity. Suitable dosage ranges are 1–200 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The preparation of compounds of the invention is further illustrated in the following examples:

Hereinafter, TLC is thin layer chromatography, THF is tetrahydrofuran, TFA is trifluoracetic acid and mp is melting point. Where melting points are given, these are uncorrected. The structures of the compounds are confirmed by assignment of NMR spectra (from which representative peaks are quoted) and by microanalysis where appropriate. Compounds used as starting materials are either known compounds or compounds which can be prepared by methods known per se. Column chromatography was carried out on Merck silica gel 60 (Art 9385). HPLC was carried out on a Waters or Merck chromatograph with a multiwavelength detector and a reversed phase C18 column (250×4 mm, 5 μm, 100 Å; eluent flow rate 1 mL/min at 35° C). Retention times are given in minutes.

EXAMPLE 1

(Method A)

2-Chloro-N-(1-phenoxy-2-propyl)adenosine

The title compound was prepared by reacting 1-phenoxy-2-propylamine (16.62 g, 0.11 mol) with 9-(2,3,5-tri-O-acetyl-β-D-ribofuranosyl)-2,6-dichloro-9H-purine (24.6 g, 55 mmol) in dioxan (250 ml) in the presence of triethylamine (7.23 g, 71.5 mmol) followed by deprotection of the product using a solution of sodium (0.15 g, 6.5 mmol) in methanol (250 ml). The reaction mixture was neutralized with citric acid, and treated with a mixture of ethyl acetate (300 ml) and water (200 ml). The ethyl acetate phase was separated, dried (MgSO$_4$) and evaporated before being purified by flash chromatography on silica gel, eluting initially with dichloromethane, and later with a mixture of dichloromethane and ethanol (9:1). This provided the title 2-chloro-N-(1-phenoxy-2-propyl)adenosine (18.2 g, 76%)(a mixture of diastereoisomers) as an amorphous foam, $^1$H NMR (DMSO-d$_6$)δ 1.31 (3H, d, —CH$_3$), 3.53–3.59 (1H, m, H-5'$_a$), 3.64–3.71 (1H, m, H-5'$_b$), 3.95 (1H, q, H-4'), 4.06–4.20 (3H, 2 m, H-3' and —CH$_2$—), 4.54 (1H, m, H-2'), 4.65 (1H, m, —CHCH$_3$), 5.07 (1H, t, 5'-OH), 5.21, 5.50 (2H, 2d, 2'- and 3'—OH), 5.84 (1H, d, H-1'), 6.87–7.00 (3H, m, Ar—H), 7.23–7.32 (2H, t, Ar—H), 8.31–8.45 (2H, m, H-8 and N—H).

The corresponding maleate salt was prepared by dissolving the above 2-chloro-N-(1-phenoxy-2-propyl)adenosine (1.7 g, 3.9 mmol) in THF (10 ml), adding diethyl ether (60 ml) followed by maleic acid (0.45 g, 3.9 mmol). The residue on evaporation was treated with diethyl ether (50 ml) whereupon the maleate salt precipitated and was collected by filtration (1.15 g), m.p. 102°–104° C.

C$_{23}$H$_{26}$ClN$_5$O$_7$ requires C, 50.0; H, 4.7; N, 12.7. Found: C, 50.3; H, 4.9; N, 12.7%.

EXAMPLE 2

(Method A)

2-Chloro-N-[(R)-1-phenoxy-2-propyl]adenosine (R)-N-(tert-Butoxycarbonyl)-2-amino-1-propanol (R)-2-Amino-1-propanol (15.0 g, 200 mmol) was dissolved in 1N sodium hydroxide (198 ml) and THF (85 ml) was introduced. The reaction mixture was cooled to 0° C. and a solution of di-tert-butyl dicarbonate (52.4 g, 240 mmol) in THF (230 ml) was added dropwise over 30 min. The reaction mixture was stored at 4° C. for 72 h., allowed to reach room temperature and filtered. The filtrate was evaporated to remove THF and the aqueous phase was extracted with ethyl acetate (2×200 ml). The combined extracts were dried (MgSO$_4$), evaporated and the crude product was dissolved in dichloromethane (100 ml) and extracted into water (5×200 ml). The combined aqueous extracts were evaporated in vacuo. The resultant oil crystallised whilst standing at room temperature to provide the required alcohol (15.35 g, 44%), mp 59°–61° C., $^1$H NMR (DMSO-d$_6$)δ 1.15 (3H, d, —CHCH$_3$), 1.45 (9H, s, butyl-CH$_3$), 3.50 (1H, dd, —CH$_2$a-), 3.65 (1H, dd, —CH$_2$b-), 3.70–3.80 (1H, m, CH).

(R)-N-(tert-Butoxycarbonyl)-1-phenoxy-2-propylamine (R)-N-(tert-butoxycarbonyl)-2-amino-1-propanol (10.0 g, 57 mmol), triphenylphosphine (22.5 g, 86 mmol) and phenol (5.4 g, 57 mmol) was dissolved in toluene (200 ml). Diethyl azodicarboxylate (14.9 g, 86 mmol) in toluene (100 ml) was slowly added keeping the temperature below 35° C. (Mitsunobu, O., Synthesis, 1981, 1; Manhas, M. S.; Hoffman, W. H.; Lal, B.; Bose, A. K., J. Chem. Soc. Perkin Trans I, 1974, 461). The resulting yellow solution was stirred for 16 h at room temperature before being washed with 1N hydrochloric acid (3×100 ml). The organic phase was dried (MgSO$_4$), evaporated in vacuo, and the residual oil was purified by flash chromatography eluting with heptane/ethyl acetate (4/1) giving the desired product (8.0 g, 59%), $^1$H NMR (DMSO-d$_6$)δ 1.10 (3H, d, —CH$_3$), 1.38 (9H, s, butyl-CH$_3$), 3.70–3.90 (3H, m, —CH—CH$_2$—), 6.85–6.95 (3H, m, Ar—H), 7.25 (2H, t, Ar—H).

(R)-1-Phenoxy-2-propylamine (R)-N-(tert-Butoxycarbonyl)-1-phenoxy-2-propylamine (8.0 g, 33 mmol) was dissolved in ethyl acetate (100 ml). A solution of hydrochloric acid (g) in ethyl acetate (6N, 100 ml) was added dropwise at room temperature. The reaction mixture was stirred at room temperature for 20 h during which time a heavy precipitate was formed. The reaction mixture was concentrated to half the original volume before the product was collected by filtration and dried in vacuo to provide the title compound as a white solid hydrochloride (4,3 g, 69%) m.p. 186°–189° C. $^1$H NMR (DMSO-d$_6$)δ 1.31 (3H, d, —CH$_3$), 3.51–3.60 (1H, m, —CH—), 4.05 (1H, dd, —CH$_2$a-), 4.12 (1H, dd, —CH$_2$b-), 6.95–7.00 (3H, m. Ar—H), 7.32 (2H, t, Ar—H).

2-Chloro-N-[(R)1-phenoxy-2-propyl]adenosine (R)-1-phenoxy-2-propylamine (4.3 g, 23 mmol) was reacted with 9-(2,3,5-tri-O-benzoyl-β-D-ribofuranosyl)-2,6-dichloro-9H-purine (11.2 g, 18 mmol) in dioxan (150 ml) in the presence of diisopropylethylamine (5.3 g, 41 mmol). The reaction mixture was stirred at room temperature for 18 h, heated at 50° C. for 4 h, and stirred at room temperature for 60 h before being filtered and evaporated. The product (after purification by flash chromatography) was debenzoylated with methanolic ammonia to provide the title 2-chloro-N-[(R)-1-phenoxy-2-propyl]adenosine (after column chromatography) as a foam (4.2 g, 64%), $^1$H NMR (DMSO-d$_6$)δ 1.31 (3H, d, —CH$_3$), 3.52–3.59 (1H, m, H-5'$_a$), 3.63–3.72 (1H, m, H-5'$_b$), 3.92–3.99 and 4.10–4.21 (4H, 2 m, H-3', H-4' and —CH$_2$—), 4.52 (1H, dd, H-2'), 4.65 (1H, m, —CH$_3$CH—), 5.07 (1H, t, 5'-OH), 5.22, 5.49 (2H, 2d, 2' and 3'-OH), 5.84 (1H, d, H-1'), 6.88–7.02 (3H, m, Ar—H), 7.24–7.33 (2H, dd, Ar—H), 8.32–8.45 (2H, s & m, H-8 and N—H).

C$_{19}$H$_{22}$ClN$_5$O$_5$ requires C, 52.4; H, 5.1; N, 16.1. Found: C, 52.0; H, 5.2; N, 15.8%.

EXAMPLE 3

(Method A)

2-Chloro-N-[(S)-1-phenoxy-2-propyl]adenosine

2-Chloro-N-[(S)-1-phenoxy-2-propyl]adenosine was prepared by the procedure described for Example 2, except that (S)-2-amino-1-propanol was used in the first step, providing the opposite diastereoisomer to Example 2. The nucleoside was obtained as a hemihydrate:

$C_{19}H_{22}ClN_5O_5 \cdot 0.5\ H_2O$ requires C, 51.8; H, 5.2; N, 15.9. Found: C, 51.8; H, 5.3; N, 15.6%.

EXAMPLE 4

(Method A)

2-Chloro-N-(2-phenoxyethyl)adenosine

The title compound was prepared by reacting 2-phenoxyethylamine hydrochloride (0.80 g, 4.6 mmol) with 9-(2,3,5-tri-O-benzoyl-β-D-ribofuranosyl)-2,6-dichloro-9H-purine (2.0 g, 3.2 mmol) in dioxan (25 ml) in the presence of triethylamine (1.0 g, 9.6 mmol) followed by deprotection of the purified product using methanolic ammonia to provide the title nucleoside (0.75 g, 60%) (following flash chromatography) as an amorphous foam, $^1$H NMR (DMSO-$d_6$)δ 3.52–3.59 (1H, m, H-5'$_a$), 3.64–3.71 (1H, m, H-5'$_b$), 3.82 (2H, q, —OH$_2$—), 3.96 (1H, q, H-4'), 4.14 (1H, m, H-3'), 4.52 (1H, q, H-2'), 5.12 (1H, t, 5'-OH), 5.25, 5.54 (2H, 2d, 2'- and 3'-OH), 5.85 (1H, d, H-1'), 6.92–7.02 (3H, m, Ar—H), 7.26–7.34 (2H, t, Ar—H), 8.46 (1H, m, H-8), 8.56 (1H, br, t, N—H).

$C_{18}H_{20}ClN_5O_5 \cdot 0.75\ H_2O$ requires C, 49.7; H, 5.0; N, 16.1. Found: C, 49.7; H, 5.0; N, 15.7%.

EXAMPLE 5

(Method A)

2-Chloro-N-[(R)-1-phenyl-2-propyl]adenosine

The title compound was prepared by reacting L-amphetamine (0.49 g, 3.6 mmol) with 9-(2,3,5-tri-O-benzoyl-β-D-ribofuranosyl)-2,6-dichloro-9H-purine (1.9 g, 3.0 mmol) in dioxan (25 ml) in the presence of diisopropylethylamine (0.58 g, 4.5 mmol) followed by deprotection of the purified product using methanolic ammonia. Evaporation of the reaction mixture provided a gummy residue which crystallized on addition of dichloromethane (10 ml), to provide the title compound (0.26 g, 38%) as a solid, m.p. 132.5°–135.5° C. A further sample of the title compound (0.26 g) was obtained by flash chromatography of the mother liquors. $^1$H NMR (DMSO-$d_6$)δ 1.22 (3H, d, —CH$_3$), 2.67–2.79 & 2.92–3.03 (2H, 2m, —CH$_2$—), 3.51–3.58 (1H, m, H-5'$_a$), 3.62–3.68 (1H, m, H-5'$_b$), 3.94 (1H, q, H-4'), 4.12 (1H, m, H-3'), 4.41–4.54 (2H, m, H-2' and CH$_3$CH—), 5.06 (1H, t, 5'-OH), 5.22, 5.49 (2H, 2d, 2' and 3'-OH), 5.82 (1H, d, H-1'), 7.10–7.33 (5H, m, Ar—H), 8.28–8.44 (2H, m, H-8 and N—H).

$C_{19}H_{22}ClN_5O_4 \cdot 0.5\ H_2O$ requires C, 53.2; H, 5.4; N, 16.3. Found: C, 53.3; H, 5.4; N, 16.3%.

EXAMPLE 6

(Method A)

2-Chloro-N-(1-phenyl-3-butyl)adenosine

3-Amino-1-phenylbutane (0.67 g, 3.6 mmol) was reacted with 9-(2,3,5-tri-O-benzoyl-β-D-ribofuranosyl)-2,6-dichloro-9H-purine (1.9 g, 3 mmol) in dioxan (25 ml) in the presence of diisopropylethylamine (0.58 g, 4.5 mmol). The reaction mixture was stirred at room temperature for 18 h, filtered and evaporated. The product (after purification by flash chromatography) was debenzoylated with methanolic ammonia to provide the title 2-chloro-N-(1-phenyl-3-butyl)adenosine (mixture of diastereoisomers) as a foam (0.72 g, 56%), $^1$H NMR (DMSO-$d_6$)δ 1.12 (3H, d, —CH$_3$), 3.53–3.61 (1H, m, H-5'$_a$), 3.64–3.72 (1H, m, H-5'$_b$), 3.93–3.99 (1H, m, H-4'), 4.11–4.17 (1H, m, H-3'), 4.22–4.36 (1H, m, —CH$_2$CH—), 4.53 (1H, dd, H-2'), 4.65 (1H, m, —CH$_3$CH—), 5.10 (1H, t, 5'-OH), 5.25, 5.51 (2H, 2d, 2' and 3'-OH), 5.83 (1H, d, H-1'), 7.12–7.30 (5H, m, Ar—H), 8.28–8.37 (1H, m, N—H), 8.40 (1H, s, H-8).

$C_{20}H_{24}ClN_5O_4 \cdot H_2O$ requires C, 53.2; H, 5.8; N, 15.5. Found: C, 53.9; H, 5.7; N, 15.6%.

EXAMPLE 7

(Method A)

N-(1-Phenoxy-2-propyl)adenosine

1-Phenoxy-2-propylamine (0.33 g, 2.18 mmol) was reacted with 6-chloropurine riboside (i.e. 9-β-D-ribofuranosyl-9H-purine)(0.5 g, 1.7 mmol) in dioxan (30 ml) in the presence of diisopropylethylamine (0.28 g, 2.2 mmol). The reaction mixture was heated at reflux for 5 h, cooled and evaporated. The residue was purified by flash chromatography on silica gel to provide the N-(1-Phenoxy-2-propyl)adenosine (a mixture of diastereoisomers) as a foam (0.06 g, 7%), $^1$H NMR (DMSO-$d_6$)δ 1.32 (3H, d, —CH$_3$), 3.52–3.60 (1H, m, H-5'$_a$), 3.64–3.71 (1H, m, H-5'$_b$), 3.93–3.99 and 4.12–4.20 (4H, 2m, m, H-4', H-3' and —CH$_2$—), 4.62 (1H, q, H-2'), 4.68–4.82 (1H, m, —CHCH$_3$), 5.40 (1H, t, 5'-OH), 5.20, 5.45 (2H, 2d, 2'- and 3'-OH), 5.90 (1H, d, H-1'), 6.88–6.98 (3H, m, Ar—H), 7.23–7.31 (2H, t, Ar—H), 7.85, 8.21, 8.38 (3H, 3s, H-2, H-8 and N—H).

EXAMPLE 8

(Method A)

2-Amino-N-(1-phenoxy-2-propyl)adenosine

1-Phenoxy-2-propylamine (2.90 g, 19.2 mmol) and 9-(2,3,5-tri-O-acetyl-β-D-ribofuranosyl)-2-amino-6-chloro-9H-purine (6.94 g, 16.2 mmol) were dissolved in dioxan (50 ml) and triethylamine (4.5 ml, 33.2 mmol) was introduced. After stirring the reaction mixture for 18 h at room temperature, diisopropylethylamine (2.08 g, 16.1 mmol) was added and the solution was heated at 80° C. for 100 h. Following column column chromatography, a 1.3 g sample of the resultant 2',3',5'-tri-O-acetyl-2-amino-N-(1-phenoxy-2-propyl)adenosine was deprotected using saturated methanolic ammonia (50 ml). The reaction mixture was evaporated, and the residue dissolved in in a mixture of ethyl acetate (150 ml) and water (150 ml). The phases were separated and the ethyl acetate phase was washed with water (2×150 ml). The ethyl acetate phase was then extracted with pH 2 dilute hydrochloric acid, and this acidic aqueous phase was washed with ethyl acetate (2×100 ml), and basified with sodium bicarbonate solution before extraction with ethyl acetate (100 ml). The ethyl acetate phase was was dried (MgSO$_4$) and evaporated to give the title compound (0.43 g, 33%) a mixture of diastereoisomers as an amorphous foam, $^1$H NMR (DMSO-$d_6$)δ 1.28 (3H, d, —CH$_3$), 3.49–3.57 (1H, m, H-5'$_a$), 3.61–3.68 (1H, m, H-5'$_b$), 3.85–3.94 and 4.07–4.15 (4H, 2m, m, H-4', H-3' and —CH$_2$—), 4.50 (1H, q, H-2'), 4.68 (1H, br, —CHCH$_3$), 5.11, 5.36 (2H, 2d, 2'- and 3'-OH), 5.40 (1H, t, 5'-OH) 5.73 (1H, d, H-1'), 5.83 (1H, br, —NH$_2$), 6.88–6.96 (3H, m, Ar—H), 7.22–7.31 (2H, t, Ar—H), 7.95 (1H, s, H-8).

$C_{19}H_{24}ClN_5O_5 \cdot 0.75\ H_2O$ requires C, 53.1; H, 6.0; N, 19.5. Found: C, 53.0; H, 6.0; N, 19.2%.

EXAMPLES 9 and 10

(Method A)

N-[(1R, Trans)-2-hydroxycyclopentyl]adenosine and N-[(1S, Trans)-2-hydroxycyclopentyl]adenosine Trans-2-hydroxycyclopentylamine (0.35 g, 3.46 mmol) (prepared by reaction of cyclopentene oxide with ammonia in a sealed vessel: see example 11) was reacted with 6-chloropurine riboside (i.e. 9-β-D-ribofuranosyl-9H-purine) (0.5 g, 1.7 mmol) in dioxan (30 ml) in the presence of triethylamine (0.93 g, 9 mmol). The reaction mixture was heated at 100° C. for 70 h, cooled and evaporated. The resultant residue was purified by flash chromatography eluting with a mixture of ethyl acetate and methanol (19:1). The fractions found to contain the highest amounts of N-[(1R, trans)-2-hydroxycyclopentyl]adenosine following HPLC examination, were combined and evaporated to a solid (0.17 g). Recrystallisation from methanol provided the pure N-[(1R, trans)-2-hydroxycyclopentyl]adenosine (0.11 g, 18%) mp 233°–235° C. $^1$H NMR (DMSO-$d_6$)δ 1.43–2.12 (6H, 4m, —CH$_2$CH$_2$ CH$_2$—), 3.52–3.59 (1H, m, H-5'$_a$), 3.54–3.71 (1H, m, H-5'$_b$), 3.97 (1H, q, H-4'), 4.07 (1H, br, —CHOH) 4.15 (1H, q, H-3'), 4.61 (1H, q, H-2'), 4.87, 5.21, 5.41–5.47 (4H, d & 3m, OH groups), 5.89 (1H, d, H-1'), 7.75 (1H, br d, —NH), 8.21 and 8.37 (H-2 and H-8).

The mother liquors from the above recrystallisation were evaporated and purified by short path chromatography on silica gel (Art. 7729) and the product recrystallised to provide N-[(1S, trans)-2-hydroxycyclopentyl]adenosine (0.05 g, 4%), $^1$H NMR (DMSO-$d_6$)δ 1.44–2.13 (6H, 4m, —CH$_2$CH$_2$CH$_2$—), 3.52–3.59 (1H, m, H-5'$_a$), 3.54–3.71 (1H, m, H-5'$_b$), 3.96 (1H, q, H-4'), 4.15 (1H, q, H-3'), 4.60 (1H, q, H-2'), 5.20, 5.41–5.47 (3H, d & m, 2', 3' and 5'-OH), 5.88 (1H, d, H-1'), 7.75 (1H, br d, —NH), 8.19 and 8.36 (H-2 and H-8).

EXAMPLE 11

(Method A)

2-Chloro-N-(cis-2-phenoxycyclopentyl)adenosine trans-N-(tert-Butyloxycarbonyl)-2-hydroxycyclopentylamine This compound was prepared as a mixture of enantiomers by reaction of cyclopentene epoxide (8.0 g, 95.1 mmol) with a 25% aqueous ammonia solution (35 ml) in a sealed glass vessel at 110° C. for 1.5 h. The reaction mixture was cooled and evaporated to half its original volume before 1N sodium hydroxide solution (95 ml) and THF (100 ml) were introduced at 0° C. A solution of di-tert-butyl dicarbonate (21.8 g, 99.6 mmol) in THF (50 ml) was added dropwise and the reaction mixture stirred at room temperature for 18 h. The phases were separated and the aqueous phase was washed with ethyl acetate (100 ml). The organic phases were combined and washed with saturated brine (100 ml), dried (MgSO$_4$) and evaporated. The solid residue was recrystallised from a 10:1 mixture of heptane and ethyl acetate (55 ml) to provide an analytical sample of trans-N-(tert-butyloxycarbonyl)-2-hydroxycyclopentylamine (4.06 g, 21%), mp 103°–105° C.

$C_{10}H_{19}NO_3$ requires C, 59.7; H, 9.5; N, 7.0. Found: C, 59.6; H, 9.8; N, 7.0%.

The above trans-N-(tert-butyloxycarbonyl)-2-hydroxycyclopentylamine was converted into cis-2-phenoxy-cyclopentyl-amine by the sequence of reactions described in Example 2 (i.e. phenyl ether formation by the Mitsunobu procedure resulting in inversion at the 2-position, followed by acidic hydrolysis of the BOC- group using TFA).

cis-2-Phenoxycyclopentylamine (0.75 g, 4.23 mmol) was combined with 9-(2,3,5-tri-O-benzoyl-β-D-ribofuranosyl)-2,6-dichloro-9H-purine (2.95 g, 4.7 mmol) and triethylamine (0.64 g, 6.3 mmol) in dioxan (30 ml) and stirred for 50 h. The reaction mixture was filtered, evaporated and the residue dissolved in ethyl acetate and washed with water (2×50 ml). The organic phase was dried (MgSO$_4$), evaporated and the residue coevaporated to give cis-2',3',5'-tri-O-benzoyl-2-chloro-N-(2-phenoxycyclopentyl)adenosine (3.1 g, 90%) as an amorphous foam, which was deprotected using saturated methanolic ammonia (50 ml). After 70 h at room temperature the reaction mixture was evaporated and the residue purified by flash chromatography on silica gel, eluting with a mixture of dichloromethane and methanol (19:1). The title cis-2-chloro-N-(2-phenoxycyclopentyl)adenosine (0.925 g, 53%) was obtained as an amorphous foam (a 1:1 mixture of diastereoisomers), $^1$H NMR (DMSO-$d_6$)δ 1.58–2.15 (6H, 3m, —CH$_2$CH$_2$CH$_2$—), 3.51–3.60 (1 H, m, H-5'$_a$), 3.62–3.71 (1H, m, H-5'$_b$), 3.95 (1H, br q, H-4'), 4.12 (1H, br q, H-3'), 4.46–4.62 (2H, m, H-2' and —CH), 4.82–4.89 (1H, m, —CH), 5.07 (1H, br t, 5'-OH), 5.22, 5.49 (2H, 2d, 2'- and 3'-OH), 5.83 (1H, d, H-1'), 6.80–6.91 (3H, m, Ar—H), 7.15–7.24 (2H, t, Ar—H), 7.99, 8.22 (1H, d & m, N—H), 8.41, 8.45 (1 H, 2s, H-8).

$C_{21}H_{24}ClN_5O_5 \cdot 0.5\ H_2O$ requires C, 53.6; H, 5.4; N, 14.9. Found: C, 53.5; H, 5.3; N, 14.7%.

EXAMPLE 12

(Method A)

Trans-2-chloro-N-2-phenoxycyclopentyl)adenosine

Cis-N-(tert-butyloxycarbonyl)-2-hydroxycyclopentylamine

Trans-N-(tert-butyloxycarbonyl)-2-hydroxycyclopentylamine (24.7 g, 123 mmol)(prepared as described in Example 11) was dissolved in THF (500 ml) and 4-nitrobenzoic acid (20.51 g, 123 mmol) was added, followed by triphenylphosphine (48.28 g, 184 mmol). A solution of diethylazodicarboxylate (32.06 g, 184 mmol) in THF (250 ml) was introduced dropwise. The reaction mixture was stirred for 18 h at room temperature, evaporated and purified by flash chromatography eluting with a mixture of cycohexane and ethyl acetate (4:1) to provide the intermediate 4-nitrobenzoyl ester as a solid (25.5 g), TLC $R_f$ 0.52 [SiO$_2$: cyclohexane/ethyl acetate (1:1)]. This ester was suspended in a mixture of a mixture of methanol (180 ml) and 25% aqueous ammonia solution (20 ml) and the mixture was stirred at room temperature for 70 h before evaporation to a residue. Purification by flash chromatography eluting with a mixture of cycohexane and ethyl acetate (4:1) provided fractions containing the title compound which crystallised on evaporation to afford cis-N-(tert-butyloxycarbonyl)-2-hydroxycyclopentylamine as a solid (11.0 g, 44%), mp 64°–65° C.

This cis-N-(tert-butyloxycarbonyl)-2-hydroxycyclopentylamine was converted into trans-2-phenoxycyclopentylamine hydrochloride by Mitsunobu phenyl ether formation and deprotection—the methods described in Example 2.

9-(2,3,5-Tri-O-benzoyl-β-D-ribofuranosyl)-2,6-dichloro-9H-purine (3.0 g, 4.7 mmol) was dissolved in dioxan (30 ml) and trans-2-phenoxycyclopentylamine hydrochloride (0.95 g, 4.4 mmol) was added followed by triethylamine (0.64 g, 6.3 mmol). The reaction mixture was stirred at room temperature for 72 h and purified by flash chromatography on silica gel to provide a foam to which saturated methanolic ammonia (100 ml) was added. After 16 h at room temperature, the reaction mixture was evaporated and purified by flash chromatography to provide the title trans-2-chloro-N-(2-phenoxycyclopentyl)adenosine (0.70 g, 35%) as an amorphous foam (a mixture of diastereoisomers), $^1$H NMR (DMSO-d$_6$), δ 1.56–2.30 (6H, 3m, —CH$_2$CH$_2$CH$_2$—), 3.52–3.60 (1H, m, H-5'$_a$), 3.63–3.71 (1H, m, H-5'$_b$), 3.96 (1H, q, H-4'), 4.13 (1H, q, H-3'), 4.50–4.61 (2H, m, H-2' and —CH), 4.82–4.89 (1H, m, —CH), 5.08 (1H, t, 5'-OH), 5.23, 5.49 (2H, 2d, 2'- and 3'-OH), 5.83 (1H, d, H-1'), 6.90, 7.07 and 7.25 (5H, t,d,t, Ar—H), 8.43 (1H, s, H-8), 8.60 (1H, d, N—H).

C$_{21}$H$_{24}$ClN$_5$O$_5$ 0.5 H$_2$O requires C, 53.6; H, 5.4; N, 14.9. Found: C, 53.4; H, 5.5; N, 14.5%.

EXAMPLE 13

(Method A)

2-Chloro-N-[(R)-1-hydroxy-2-propyl]adenosine (R)-2-Amino-1-propanol (0.23 g, 3.0 mmol), 9-(2,3,5-tri-O-benzoyl-β-D-ribofuranosyl)-2,6-dichloro-9H-purine (1.7 g, 2.7 mmol) and triethylamine (0.30 g, 3.0 mmol) were dissolved in dioxan (20 ml) and stirred for 200 h at room temperature. Following purification by column chromatography, the resultant 2',3',5'-tri-O-benzoyl-2-chloro-N-[(R)-1-hydroxy-2-propyl]adenosine was deprotected using methanolic ammonia to provide the title 2-chloro-N-[(R)-1-hydroxy-2-propyl]adenosine as an amorphous foam (0.5 g, 54%), $^1$H NMR (DMSO-d$_6$)δ 1.17 (3H, d, —CH$_3$), 3.35–3.72 (4H, m, H-5'$_a$, H-5'$_b$ and —CH$_2$—), 3.96 (1H, q, H-4'), 4.14 (1H, m, H-3'), 4.52 (1H, dd, H-2'), 5.08 (1H, t, 5'-OH), 5.22, 5.49 (2H, 2d, 2' and 3'-OH), 5.83 (1H, d, H-1'), 8.0 (1H, d, N—H) 8.40 (1H, s, H-8).

C$_{13}$H$_{17}$ClN$_5$O$_5$.0.75 H$_2$O requires C, 41.9; H, 5.0; N, 18.8. Found: C, 42.1; H, 5.2; N, 15.8%.

EXAMPLE 14

(Method A)

2-Chloro-N-[(R)-1-phenylthio-2-propyl]adenosine (R)-N-tertbutyloxycarbonyl-1-phenylthio-2-propylamine Thiophenol (1.5 g, 14 mmol) was dissolved in dry THF (100 ml) and a 60% oil dispersion of sodium hydride (0.30 g, 14 mmol) was added in portions under nitrogen. After stirring for 15 min. at room temperature, the mesylate ester of N-tert-butoxycarbonyl-2-hydroxypropylamine (3.2 g, 14 mmol) was added in three portions and the reaction mixture was heated at 70° C. for 18 h. After cooling, water (30 ml) was added, the aqueous phase was separated and washed with dichloromethane (50 ml). The combined organic phases were dried (MgSO$_4$) and evaporated to give (R)-N-tertbutyloxycarbonyl-1-phenylthio-2-propylamine as a fawn oil (3.2 g, 85%), TLC R$_f$ 0.64 [SiO$_2$: heptane/ethyl acetate (1:1)].

This (R)-N-(tert-butoxycarbonyl)-1-phenylthio-2-propylamine was converted into (R)-1-phenylthio-2-propylamine hydrochloride by acidic hydrolysis using the method described in Example 2.

(R)-1-Phenylthio-2-propylamine (0.4 g, 1.96 mmol) was reacted with 9-(2,3.5-tri-O-benzoyl-β-D-ribofuranosyl)- 2,6-dichloro-9H-purine (1.2 g, 1.9 mmol) in dioxan (15 ml) in the presence of triethylamine (0.4 g, 4 mmol). The reaction mixture was stirred at room temperature for 72 h, heated at 50° C. for 24 h, cooled, filtered and evaporated. The product (after purification by flash chromatography) was debenzoylated with methanolic ammonia to provide the title 2-chloro-N-[(R)-1-phenylthio-2-propyl]adenosine (after column chromatography) as a foam (0.47 g, 52%), $^1$H NMR (DMSO-d$_6$)δ 1.34 (3H, d, —CH$_3$), 3.01 (1H, dd, —C—H), 3.52–3.60 (1H, m, H-5'$_a$), 3.62–3.72 (1H, m, H-5'$_b$), 3.95 (1H, q, H-4'), 4.13 (1H, m, H-3'), 4.30–4.45 (1H, m, —C—H), 4.53 (1H, m, H-2'), 5.09, 5.22, 5.50 (3H, 3 br, 2', 3' and 5'-OH), 5.84 (1H, d, H-1'), 7.19 (1H, t, Ar—H), 7.30 (2H, t, Ar—H), 7.45 (2H, d, Ar—H), 8.29–8.45 (2H, s & m, H-8 and N—H).

C$_{19}$H$_{22}$ClN$_5$O$_4$S requires C, 50.5; H, 4.9; N, 15.5. Found: C, 50.6; H, 5.1; N, 15.2%.

EXAMPLE 15

(Method A)

(R)-2-Chloro-N-[1-(4-fluorophenoxy)-2-propyl]adenosine (R)-1-(4-fluorophenoxy)-2-propylamine (0.29 g, 1.4 mmol)(prepared from 4-fluorophenol by the method described in example 2) was reacted with 9-(2',3',5'-tri-O-benzoyl-β-D-ribofuranosyl)-2,6-dichloro-9H-purine (0.89 g, 1.4 mmol) in dioxan (30 ml) in the presence of triethylamine (0.42 g, 3 mmol). The reaction mixture was stirred at room temperature for 18 h, and heated at 60° C. for 4 h. The reaction mixture was filtered and evaporated to a residue which was purified by flash chromatography. The resultant 2',3',5'-tri-O-benzoyl-2-chloro-N-[(R)-1-(4-fluorophenoxy)-2-propyl]adenosine was deprotected using methanolic ammonia to provide the title 2-chloro-N-[(R)-1-(4-fluorophenoxy)-2-propyl]adenosine (0.21 g, 40%)(after column chromatography), mp 172°–173° C.; $^1$H NMR (DMSO-d$_6$)δ 1.29 (3H, d, —CH3), 3.52–3.60 (1H, m, H-5'$_a$), 3.64–3.72 (1H, m, H-5'$_b$), 3.92–4.00 (2H, m, H-4' and —C—H), 4.05–4.20 (2H, m, H-3' and —C—H), 4.53 (1H, m, H-2'), 4.65 (1H, m, —CH$_3$CH—), 5.08, 5.24, 5.50 (3H, 3 br, 2', 3' and 5'-OH), 5.86 (1H, d, H-1'), 6.89–7.15 (4H, 2 m, Ar—H), 8.30–8.46 (2H, m, H-8 and N—H).

C$_{19}$H$_2$ClFN$_5$O$_5$ requires C, 49.8; H, 4.7; N, 15.3. Found: C, 49.4; H, 4.7; N, 14.9%.

EXAMPLE 16

(Method A)

2-Chloro-N-[(R)-2-phenoxy-1-propyl]adenosine (R)-2-Phenoxy-1-propylamine (0.6 g, 2.9 mmol) (prepared by the method described in example 2) was reacted with 9-(2,3,5-tri-O-benzoyl-β-D-ribofuranosyl)-2,6-dichloro-9H-purine (1.5 g, 2.4 mmol) in dioxan (20 ml) in the presence of triethylamine (0.5 g, 5.3 mmol). The reaction mixture was stirred at room temperature for 72 h before being filtered and evaporated. The product, following purification by flash chromatography, was treated with saturated methanolic ammonia (30 ml) for 18 h and evaporated to provide a solid residue. This solid was washed thoroughly with dichloromethane to provide the title 2-chloro-N-[(R)-2-phenoxy-1-propyl]adenosine (0.7 g, 65%), mp 175°–177° C., $^1$H NMR (DMSO-d$_6$)δ 1.39 (3H, d, —CH$_3$), 3.56 (1H, ABX, H-5'$_a$), 3.68 (1H, m, H-5'$_b$), 3.33–3.40 (1H, m, —C—H), 3.83–3.92 (1H, —C—H), 3.96 (1H, q, H-4'), 4.14 (1H, m, H-3'), 4.53 (1H, dd, H-2'), 4.70 (1H, q, —C—H), 5.08, 5.34, 5.50 (3H, 3 br, 2', 3' and 5'-OH), 5.85 (1H, d, H-1'), 6.90 (1H, t, Ar—H), 7.11 (2H, d, Ar—H), 7.28 (2H, t, Ar—H), 8.45 (1H, s, H-8), 8.63 (1H, t, N—H).

$C_{19}H_{22}ClN_5O_5$ requires C, 52.4; H, 5.1; N, 16.1. Found: C, 52.5; H, 5.1; N, 15.9%.

EXAMPLE 17

(Method A)

2-Chloro-N-[2-(phenylmethoxy)ethyl]adenosine

The title compound was prepared by reacting 2-(phenylmethoxy)ethylamine hydrochloride (0.51 g, 2.7 mmol) with 9-(2,3,5-tri-O-benzoyl-β-D-ribofuranosyl)-2,6-dichloro-9H-purine (1.43 g, 2.25 mmol), followed by debenzoylation of the purified product using methanolic ammonia to provide the title 2-chloro-N-[2-(phenylmethoxy)ethyl]adenosine (0.38 g, 44%)(after column chromatography) as a solid, mp 115°–124° C., $^1$H NMR (DMSO-d$_6$)δ 3.50–3.58 (1H, m, H-5'$_a$), 3.60–3.70 (4H, m, H-5'$_b$, —CH$_2$— and —CH—), 3.95 (1H, q, H-4'), 4.04–4.16 (2H, m, H-3' and —CH—), 4.52 (1H, br s, H-2' and —CH$_2$—), 5.07 (1H, t, 5'-OH), 5.21, 5.50 (2H, 2d, 2'- and 3'-OH), 5.84 (1H, d, H-1'), 7.22–7.36 (5H, m, Ar—H), 8.25–8.40 (2H, m, H-8 and N—H).

$C_{19}H_{22}ClN_5O_5$. 0.1 H$_2$O requires C, 52.1; H, 5.1; N, 16.0. Found: C, 51.8; H, 5.3; N, 15.6%.

EXAMPLE 18

(Method A)

2-Fluoro-N-[(R)-1-phenoxy-2-propyl]adenosine 9-(2,3,5-Tri-O-acetyl-β-D-ribofuranosyl)-6-chloro-2-fluoro-9H-purine (1.03 g, 2.38 mmol) PCT Publication No. WO 93/08206, (R)-1-phenoxy-2-propylamine (0.36 g, 2.38 mmol) and triethylamine (0.29 g, 0.28 mmol) in dioxan (20 ml) were stirred at room temperature for 18 h. The reaction mixture was filtered and evaporated to a residue which was purified by flash chromatography. The resultant 2',3',5'-tri-O-acetyl-2-fluoro-N-[(R)-1-phenoxy-2-propyl]adenosine was deprotected using methanolic ammonia to provide the title 2-fluoro-N-[(R)-1-phenoxy-2-propyl]adenosine (0.28 g, 23%)(after column chromatography), mp 148°–150° C.; $^1$H NMR (DMSO-d$_6$)δ 1.33 (3H, d, - 3.59 (1H, m, H-5'$_a$), 3.63–3.71 (1H, m, H-5'$_b$), 3.92–3.99 (2H, m, H-4' and —C—H), 4.10–4.18 (2H, m, H-3' and —C—H), 4.51 (1H, q, H-2'), 4.61 (1H, m, —CH$_3$CH—), 5.06 (1H, t, 5'-OH), 5.22, 5.48 (2H, 2d, 2' and 3'-OH), 5.82 (1H, d, H-1'), 6.89–6.97 (3H, m, Ar—H), 7.25–7.30 (2H, t, Ar—H), 8.39 (1H, s, H-8), 8.49 (1H, d, N—H).

$C_{19}H_{22}FN_5O_5$ requires C, 54.4; H, 5.3; N, 16.7. Found: C, 54.7; H, 5.5; N, 16.4%.

EXAMPLE 19

(Method B)

2-Methoxy-N-[R-1-phenoxy-2-propyl]adenosine

2-Methoxy-N-[(R)-1-phenoxy-2-propyl]adenosine was prepared by reacting 2-chloro-N-((R)1-phenoxy-2-propyl)adenosine (Example 2)(0.30 g, 0.69 mmol) with a mixture of sodium hydroxide (0.32 g, 8.0 mmol) and methanol (15 ml) in a sealed vessel at 80°–90° C. for 4 h. The cooled reaction mixture was neutralised with concentrated hydrochloric acid and evaporated to dryness. Water (30 ml) was added and the mixture was extracted with dichloromethane (2×30 ml). The combined extracts were dried (MgSO$_4$) and coevaporated with dichloromethane (30 ml), giving the title compound as a foam (0.19 g, 60%), $^1$H NMR (DMSO-d$_6$)δ 1.32 (3H, d, —CHCH$_3$), 3.55 (1H, m, H-5'$_a$), 3.65 (1H, m, H5'$_b$), 3.72 (3H, s, —CH$_3$), 3.91–3.99 and 4.10–4.20 (4H, 2 m, H-3', H-4' and —CH$_2$—), 4.51 (1H, dd, H-2'), 4.67 (1H, m, —CHCH$_3$), 5.84 (1H, d, H-1'), 6.89–6.98 (3H, m, Ar—H), 7.26 (2H, dd, Ar—H) 8.12 (1H, br, —NH), 8.46 (1H, s, H-8).

EXAMPLE 20

(Method A)

N-(2-Methoxyethyl)adenosine

The title compound was prepared by the procedure described in example 7 by reacting 2-methoxyethylamine hydrochloride (0.27 g, 3.6 mmol) with 6-chloropurine riboside (i.e. 9-β-D-ribofuranosyl-6-chloro-9H-purine)(1.0 g, 3.5 mmol) in dioxan (30 ml) at room temperature for 72 h with triethylamine (1.04 ml, 7.5 mmol) present. The reaction mixture was filtered and evaporated and the resultant residue was recrystallised from methanol (100 ml) to provide the title compound (0.80 g, 82%) as a solid, mp 151°–152° C., $^1$H NMR (DMSO-d$_6$)δ 3.26 (3H, s, —CH$_3$), 3.50–3.58 (3H, m, H-5'$_a$ and —CH$_2$—), 3.60–3.70 (3H, m, H-5'$_b$, and —CH$_2$—), 3.96 (1H, q, H-4'), 4.14 (1H, dd, H-3'), 4.60 (1H, dd, H-2') 5.20, 5.45 (2H, 2d, 2'- and 3'-OH), 5.42 (1H, t, 5'-OH) 5.87 (1H, d, H-1'), 7.80 (1H, br s, —NH) 8.22, 8.35 (2H, 2s, H-2 and H-8).

$C_{13}H_{19}N_5O_5$ requires C, 48.0; H, 5.9; N, 21.5. Found: C, 47.8; H, 5.9; N, 21.3%.

EXAMPLE 21

(Method A)

2-Chloro-N-[(2-methoxyphenyl)methyl]adenosine

The title compound was prepared by reacting (2-methoxyphenyl)methylamine (0.55 g, 4.0 mmol) with 9-(2,3,5-tri-O-benzoyl-β-D-ribofuranosyl)-2,6-dichloro-9H-purine (1.01 g, 1.6 mmol), followed by debenzoylation of the purified product using methanolic ammonia to provide the title 2-chloro-N-[(2-methoxyphenyl)methyl]adenosine (0.31 g, 45%)(after column chromatography) as a solid, mp 116°–119° C., $^1$H NMR (DMSO-d$_6$)δ 3.51–3.60 (1H, m, H-5'$_a$), 3.61–3.70 (1H, m, H-5'$_b$), 3.95 (1H, q, H-4'), 4.13 (1H, m, H-3'), 4.52 (1H, q, H-2'), 5.06 (1H, t, 5'-OH), 5.22, 5.50 (2H, 2d, 2'- and 3'-OH), 5.85 (1H, d, H-1'), 6.83–7.25 (4H, 2t, 2d, Ar—H), 8.43 (1H, s, H-8), 8.72 (1H, t, N—H).

EXAMPLE 22

(Method A)

2-Chloro-N-[(R)-3-methyl-1-phenoxy-2-butyl]adenosine (R)-3-methyl-1-phenoxy-2-butylamine (0.6 g, 2.8 mmol) was reacted with 9-(2,3,5-tri-O-benzoyl-β-D-ribofuranosyl)-2,6-dichloro-9H-purine (1.4 g, 2.2 mmol) in dioxan (20 ml) in the presence of triethylamine (0.5 g, 5.0 mmol). The reaction mixture was stirred at room temperature for 40 h before being filtered and evaporated. The product (after purification by flash chromatography) was debenzoylated with methanolic ammonia to provide the product (after column chromatography) as a foam which solidified on coevaporation with dichloromethane. 2-Chloro-N-[(R)-3-methyl-1-phenoxy2-butyl]adenosine (0.46 g, 44%) was obtained as a white solid, mp 95°–100° C., $^1$H NMR (DMSO-d$_6$)δ 0.95, 0.98 (6H, 2d, 2×—CH$_3$), 2.10 (1H, m, —CH(CH₃)₂), 3.53–3.60 (1H, m, H-5'$_a$), 3.63–3.71 (1H, m, H-5'$_b$), 3.95 (1H, q, H-4), 4.07–4.23 (3H, m, H-3' and —CH₂—), 4.96 (1H, m, —C—H), 4.56 (1H, q, H-2'), 5.08 (1H, t, 5'-OH), 5.23, 5.49 (2H, 2d, 2' and 3'-OH), 5.84 (1H, d, H-1'), 6.87–6.97 (3H, m, Ar—H), 7.24–7.31 (2H, dd, Ar—H), 8.36 (1H, d, —N—H), 8.40 (1H, s, H-8).

C$_{21}$H$_{26}$ClN$_5$O$_5$.0.5 H$_2$O requires C, 53.3; H, 5.8; N, 14.8. Found: C, 53.4; H, 5.7; N, 14.8%.

EXAMPLE 23

(Method A)

2-Chloro-N-[(R)-1-(2-(2-propyloxy)phenoxy)-2-propyl] adenosine (R)-1-(2-(2-Propyloxy)phenoxy)-2-propylamine (prepared from 2-(2-propyloxy)phenol by the procedure described in example 2)(0.54 g, 2.2 mmol) was reacted with 9-(2,3,5-tri-O-acetyl-β-D-ribofuranosyl)-2,6-dichloro-9Hpurine (2.0 g, 4.5 mmol) in dioxan (30 ml) in the presence of triethylamine (2.19 g, 22 mmol). The reaction mixture was stirred at room temperature for 18 h before being filtered and evaporated. The product (after purification by flash chromatography) was debenzoylated with methanolic ammonia to provide the 2-chloro-N-[(R)-1-(2-(2-propyloxy)phenoxy)-2-propyl]adenosine (after column chromatography) as a foam (0.47 g, 39%), ¹H NMR (DMSO-d$_6$)δ 1.04, 1.06 (6H, 2d, 2×—CH₃), 1.31 (3H, d, —CH₃), 3.53–3.60 (1H, m, H-5'$_a$), 3.64–3.71 (1H, m, H-5'$_b$), 3.95 (1H, q, H-4'), 3.98–4.15 (3H, 2m, H-3' and —CH₂—), 4.35 (1H, p, —C—H), 4.51 (1H, q, H-2'), 4.72 (1H, m, —C—H), 5.08 (1H, t, 5'-OH), 5.22, 5.48 (2H, 2d, 2' and 3'-OH), 5.85 (1H, d, H-1'), 6.82–7.08 (5H, m, Ar—H), 8.32 (1H, d, —N—H), 8.41 (1H, s, H-8).

C$_{22}$H$_{28}$ClN$_5$O$_6$.1.0 H$_2$O requires C, 51.6; H, 5.9; N, 13.7. Found: C, 52.0; H, 5.8; N, 13.3%.

EXAMPLE 24

(Method A)

2-Chloro-N-[(R)-1-phenylsulphonyl-2-propyl]adenosine (R)-1-Phenylsulphonyl-2-propylamine (0.4 g, 1.7 mmol) was reacted with 9-(2,3,5-tri-O-benzoyl-β-D-ribofuranosyl)-2,6-dichloro-9H-purine (1.7 g, 1.0 mmol) in dioxan (20 ml) in the presence of triethylamine (0.4 g, 4.3 mmol). The reaction mixture was stirred at room temperature for 48 h, heated at 60° C. for 4 h, cooled, filtered and evaporated. The product (after purification by flash chromatography) was debenzoylated with methanolic ammonia to provide the title 2-chloro-N-[(R)-1-phenylsulphonyl-2-propyl]adenosine (after column chromatography) as a foam (0.2 g, 24%), ¹H NMR (DMSO-d$_6$)δ 1.24 (3H, d, —CH₃), 3.45 (1H, dd, —C—H), 3.53–3.61 (2H, m, H-5'$_a$ and —C—H), 3.64–3.71 (1H, m, H-5'$_b$), 3.86 (1H, dd, —C—H), 3.97 (1H, q, H-4'), 4.14 (1H, m, H-3'), 4.53 (1H, m, H-2'), 5.09 (1H, t, 5'-OH), 5.23, 5.50 (2H, 2 d, 2' and 3'-OH), 5.83 (1H, d, H-1'), 7.45–7.82 (5H, m, Ar—H), 8.21 (1H, s, —N—H), 8.38 (1H, s, H-8).

EXAMPLE 25

(Method A)

N-[(2-methylphenyl)methyl]adenosine

The title compound was prepared by reacting (2-methylphenyl)methylamine (1.51 g, 12.5 mmol) with 6-chloropurine riboside (2.87 g, 10.0 mmol) in dioxan (100 ml) in the presence of diisopropylethylamine (1.94 g, 15.0 mmol). The reaction mixture was heated at 60° C. for 6 h, cooled, filtered and evaporated. The residue was purified by flash chromatography, eluting initially with dichloromethane, and later increasing polarity to dichloromethane/ethanol (9:1), to provide the product (2.6 g, 70%) as a solid which was recrystallised from methanol to give N-[(2-methylphenyl)methyl]adenosine as white crystals (1.75 g, 47%), mp 161.5°–163.5° C., ¹H NMR (DMSO-d$_6$)δ 2.35 (3H, s, —CH₃), 3.53–3.60 (1H, m, H-5'$_a$), 3.65–3.72 (1H, m, H-5'$_b$), 3.98 (1H, q, H-4'), 4.16 (1H, m, H-3'), 4.64 (1H, q, H-2'), 5.41 (1H, t, 5'-OH), 5.21, 5.48 (2H, 2d, 2'- and 3'-OH), 5.92 (1H, d, H-1'), 7.06–7.24 (4H, m, Ar—H), 8.20 and 8.40 (3H, s and br s, H-2, H-8 and N—H).

EXAMPLE 26

(Method A)

2-Methyl-N-[(R)-1-phenoxy-2-propyl]adenosine (R)-1-phenoxy-2-propylamine (0.56 g, 3 mmol) was reacted with 9-(2,3,5-tri-O-acetyl-β-D-ribofuranosyl)-6-chloro-2-methyl-9H-Purine (0.43 g, 1 mmol) [prepared from 2-methylinosine (Journal of Organic Chemistry, 1967, 32, 3258–3260) by standard acylation and chlorination steps] in dioxan (20 ml) in the presence of triethylamine (0.41 g, 4 mmol). The reaction mixture was heated at 50° C. for 70 h, and at 90° C. for 3 h. before being filtered and evaporated. The product (after purification by flash chromatography) was debenzoylated with methanolic ammonia to provide the title 2-methyl-N-[(R)-1-phenoxy-2-propyl]adenosine (after column chromatography) as a foam (0.21 g, 50%), ¹H NMR (DMSO-d$_6$)δ 1.30 (3H, d, —CH₃), 2.43 (3H, s, —CH₃), 3.53–3.60 (1H, m, H-5'$_a$), 3.66–3.73 (1H, m, H-5'$_b$), 3.94 (1H, dd, —C—H), 3.99 (1H, q, H-4'), 4.12–4.22 (2H, m, H-3' and —C—H), 4.54 (1H, dd, H-2'), 4.76 (1H, m, —CH₃CH—), 5.20, 5.52 (2H, 2d, 2' and 3'-OH), 5.73 (1H, t, 5'-OH), 5.87 (1H, d, H-1'), 6.90–7.31 (5H, t, m, t, Ar—H), 7.74 (1H, br d, N—H), 8.28 (1H, s, H-8).

C$_{20}$H$_{25}$ClN$_5$O$_5$.0.33 H$_2$O requires C, 57.0; H, 6.1; N, 16.6. Found: C, 57.0; H, 6.2; N, 16.8%.

Evaluation of the Compounds.

Methods for assessing adenosine receptor binding in vitro have been reviewed [Adenosine Receptors, (Cooper, D. M. F. and Londos, C., eds.) Alan R. Liss, Inc., New York, 1988, 43–62].

Evaluation of these compounds in established animal models has indicated that the compounds according to the invention possess desirable central nervous system properties. For example, they act as anticonvulsant agents, are effective in animal models of pain, and show cerebroprotective effects in laboratory test animals subjected to simulated cerebral ischaemia. In addition, the compounds may have efficacy as neuroprotective agents in cases of cerebral oedema and traumatic head injury.

Evaluation of in vitro Binding to Adenosine A1 and A2 Receptors

The affinity of the known and novel compounds described in this invention for the adenosine A1 receptor has been determined essentially as described in the literature using [³H]-R-PIA as a radioligand (Naunyn-Schmiedeberg's Archives of Pharmacology, 1980, 313, 179–187). Affinity for the A2 receptor was measured using the radioligand [³H]-CGS 21680 (European Journal of Pharmacology, 1989, 168, 243–246), and the values for representative compounds are given in table I below. In vitro receptor binding values obtained for the reference standard adenosine agonists CPA [N-(cyclopentyl)adenosine] and R-PIA [N-(1-phenyl-2-propyl)adenosine]) are included for comparison.

Method Description

DMCM Induced Seizures in Mice

In this model, seizures are induced by i.p. (intraperitoneal) dosing of methyl 6,7-dimethoxy-4-ethyl-β-carboline-3-carboxylate DMCM at 15 mg/kg.

DMCM is an inverse agonist to the benzodiazepine receptor, presumably producing seizures by decreasing the potency of inhibition of the GABA receptor/benzodiazepine receptor/chloride ionophore complex.

15 mg/kg of DMCM dissolved in 0.02N HCl (1 mg/ml) is administered i.p. in a volume of 300 μl to male NMRI mice weighing 20±2 g. This induces two different responses: a) some animals manifest a brief loss of righting reflexes or take up an upright position in which they have a mild short clonus of the upper extremities, b) other animals manifest intense clonic and tonic convulsions of all extremities often followed by death. DMCM is administered 30 min after an intraperitoneal injection of a test compound. Latency time for the presence of intense clonic and tonic convulsions and death is noted until 15 min after administration of DMCM. At least 5 doses of each test compound are tested with 8 mice per dose.

An anticonvulsive $ED_{50}$ value is determined as the dose (mg/kg) protecting 50% of the animals against clonic convulsions; some representative values are shown in table II.

The above method is a described in Petersen, E. N., Eur. J. Pharmacol. 94, 117–124, 1983; Petersen, E. N., Eur. J. Pharmacol. 195, 261–265, 1991.

Blood Pressure in Anaesthetised Rats

Test compounds are generally dissolved in DMSO and diluted in 5% chremophore/saline before being dosed to nembutal anaesthetised 200 g female Sprague Dawley rats which have not been starved or fasted. The rats are breathing spontaneously; blood pressure (BP) and heart rate (HR) is measured 5 minutes after a bolus i.v. injection. Each measurement is repeated twice. Results for representative compounds are shown in table II.

Neuroprotective Effect: Gerbil BCAO Ischemia Model.

Transient global ischaemia was produced in Mongolian gerbils (60–70 g, males) anaesthetized with 2% halothane in 70% nitrous oxide and 30% oxygen. The common carotid arteries were occluded for 5 min. and the animals were allowed to recover for 4 days. The animals were reanaesthetized, decapitated and the brains quickly removed and frozen in powdered dry ice. Coronal sections (20 μm) were taken through the brain at the level of the hippocampus and stained with cresyl violet and hematoxylineosin. The brain sections were rated for neuronal damage in the hippocampus CA1 region using a scale from 0 (undamaged) to 3 (total damage of CA1). The body temperature of all the animals was maintained at 37° C. throughout the surgery and the animals were placed in warmed boxes during the recovery period. Each experiment consisted of a drug and a vehicle control group (n=10–15). Test compounds were administered 30 min. after reperfusion.

TABLE I

| | In Vitro evaluation of the compounds | | |
|---|---|---|---|
| Adenosine agonist tested | A1 receptor binding ($K_i$, nM) | A2 receptor binding ($K_i$, nM) | Ratio A2/A1 |
| (1) | 43 | 1157 | 27 |
| (2) | 18 | 318 | 18 |
| (3) | 100 | 7413 | 74 |
| (4) | 166 | 3095 | 19 |

TABLE I-continued

| | In Vitro evaluation of the compounds | | |
|---|---|---|---|
| Adenosine agonist tested | A1 receptor binding ($K_i$, nM) | A2 receptor binding ($K_i$, nM) | Ratio A2/A1 |
| (5) | 4 | 123 | 31 |
| (6) | 36 | 802 | 22 |
| (7) | 18 | 791 | 44 |
| (8) | 123 | 2188 | 18 |
| (9) | 3.3 | 3270 | 991 |
| (10) | 3.1 | 1320 | 426 |
| (11) | 35 | 397 | 11 |
| (12) | 6 | 383 | 64 |
| (13) | 7 | 2241 | 320 |
| (14) | 15 | 893 | 60 |
| (15) | 19 | 540 | 28 |
| (17) | 340 | 7776 | 23 |
| (18) | 8 | 310 | 39 |
| (19) | 88 | 2332 | 27 |
| (20) | 77 | 2432 | 32 |
| (26) | 69 | 1200 | 17 |
| CPA | 1.6 | 173 | 108 |
| (R)-PIA | 2.0 | 134 | 67 |

TABLE II

| Pharmacological evaluation of the compounds | | |
|---|---|---|
| Compound (Example No.) | DMCM seizures $ED_{50}$(mg/kg)i.p. | % fall in BP 0.1 mg/kg i.v. |
| (1) | 3.4 | 0 |
| (2) | 3.9 | 8 |
| (4) | 13.3 | 0 |
| (6) | 3.8 | 5 |
| (8) | 24.9 | 1 |
| (10) | 0.1 | — |
| (11) | 2.0 | 15 |
| (12) | 6.7 | 25 |
| (14) | 9.9 | 15 |
| (15) | 13.6 | 16 |
| (19) | 6.7 | 22 |
| (25) | 0.5 | 45 |
| (26) | 1.9 | 15 |

We claim:

1. A method of treating epilepsy in a person in need thereof, comprising administering an effective amount of a compound, wherein the compound is selected from the group consisting of:

2-chloro-N-(1-phenoxy-2-propyl)adenosine;
2-chloro-N-[(R)-1-phenoxy-2-propyl]adenosine;
2-chloro-N-(2-phenoxyethyl)adenosine;
2-chloro-N-(1-phenyl-3-butyl)adenosine;
2-amino-N-(1-phenoxy-2-propyl)adenosine;
2-chloro-N-(cis-2-phenoxycyclopentyl)adenosine;
2-chloro-N-(trans-2-phenoxycyclopentyl)adenosine;
2-chloro-N-[(R)-1-phenylthio-2-propyl]adenosine;
(R)-2-chloro-N-[1-(4-fluorophenoxy)-2-propyl]adenosine;
2-methoxy-N-[(R)-1-phenoxy-2-propyl]adenosine;
2-methyl-N-[(R)-1-phenoxy-2-propyl]adenosine; and pharmaceutically acceptable salts thereof.

2. A method according to claim 1, wherein the compound is 2-chloro-N-(1-phenoxy-2-propyl)adenosine or a pharmaceutically acceptable salt thereof.

3. A method according to claim 1, wherein the compound is 2-chloro-N-[(R)-1-phenoxy-2-propyl]adenosine or a pharmaceutically acceptable salt thereof.

4. A method according to claim 1, wherein the compound is 2-chloro-N-(2-phenoxyethyl)adenosine or a pharmaceutically acceptable salt thereof.

5. A method according to claim 1, wherein the compound is 2-chloro-N-(1-phenyl-3-butyl)adenosine or a pharmaceutically acceptable salt thereof.

6. A method according to claim 1, wherein the compound is 2-amino-N-(1-phenoxy-2-propyl)adenosine or a pharmaceutically acceptable salt thereof.

7. A method according to claim 1, wherein the compound is 2-chloro-N-(cis-2-phenoxycyclopentyl)adenosine or a pharmaceutically acceptable salt thereof.

8. A method according to claim 1, wherein the compound is 2-chloro-N-(trans-2-phenoxycyclopentyl)adenosine or a pharmaceutically acceptable salt thereof.

9. A method according to claim 1, wherein the compound is 2-chloro-N-[(R)-1-phenylthio-2-propyl]adenosine or a pharmaceutically acceptable salt thereof.

10. A method according to claim 1, wherein the compound is (R)-2-chloro-N-[1-(4-fluorophenoxy)-2-propyl]adenosine or a pharmaceutically acceptable salt thereof.

11. A method according to claim 1, wherein the compound is 2-methoxy-N-[(R)-1-phenoxy-2-propyl]adenosine or a pharmaceutically acceptable salt thereof.

12. A method according to claim 1, wherein the compound is 2-methyl-N-[(R)-1-phenoxy-2-propyl]adenosine or a pharmaceutically acceptable salt thereof.

* * * * *